United States Patent
Kelly

[11] Patent Number: 5,526,803
[45] Date of Patent: Jun. 18, 1996

[54] MALE TRUSS

[76] Inventor: William G. Kelly, 102 Candlewood Gardens, Baldwinsville, N.Y. 13027

[21] Appl. No.: 534,010

[22] Filed: Sep. 26, 1995

[51] Int. Cl.6 .................................. A61F 5/24; A61F 6/02
[52] U.S. Cl. ........................ 128/95.1; 128/842; 128/885; 600/39
[58] Field of Search ..................... 128/95.1, 96.1, 128/842, 844, 918, 885; 604/347–353; 600/29–31

[56] References Cited

U.S. PATENT DOCUMENTS

| | | |
|---|---|---|
| 678,943 | 7/1901 | Davis ........................................ 128/885 |
| 2,581,114 | 1/1952 | Larson . |
| 3,636,948 | 1/1972 | Atchley . |
| 4,203,432 | 5/1980 | Koch . |
| 4,834,115 | 5/1989 | Stewart . |
| 4,880,016 | 11/1989 | Worth ...................................... 128/885 |
| 4,942,886 | 7/1990 | Timmons ............................... 128/885 |
| 4,971,074 | 11/1990 | Hrubetz .................................. 128/885 |
| 5,027,800 | 7/1991 | Rowland . |
| 5,244,454 | 9/1993 | Coates . |
| 5,246,015 | 9/1993 | Baber . |
| 5,421,324 | 6/1995 | Kelly . |

*Primary Examiner*—Michael A. Brown
*Attorney, Agent, or Firm*—Harris Beach & Wilcox

[57] ABSTRACT

A male truss for assisting in producing and maintaining an erection. A linear rigid member is mounted upon a loop capable of drawing the member into biasing contact against the dorsal side of the penis to restrict the flow of blood moving through the dorsal vein.

13 Claims, 6 Drawing Sheets

MALE TRUSS

BACKGROUND OF THE INVENTION

The invention relates to a male truss for aiding in producing and maintaining an erection.

As explained in U.S. Pat. No. 8,838,948 to Atchley, truss devices have been devised which are designed specifically to restrict the flow of blood back through the dorsal vein of the penis to the heart. Most of these devices are circular in form and include internal, radially extended protuberances that must be accurately positioned with regard to the dorsal vein. Accordingly, these devices are relatively difficult to fit properly and are uncomfortable to the wearer once fitted. Additionally, many of these prior art devices are bulky and tend to interfere in the wearer's ability to engage in intercourse and are difficult to clean and thus cannot be used safely more than once.

In U.S. Pat. No. 5,421,324, filed in the name of the present inventor, there is disclosed a male truss that includes a linear rigid hollow cylinder that is mounted upon an endless elastic band. The cylinder has a longitudinal slit that allows the band to be slipped inside the member. This device operates well in practice and the present invention represents an improvement over the device disclosed in the original patent.

SUMMARY OF THE INVENTION

It is therefore an object of the present invention to improve devices for achieving and maintaining an erection.

It is a further object of the present invention to provide a male truss that is easily fitted by the user to restrict the flow of blood through the dorsal vein of the penis.

A still further object of the present invention is to provide a male truss that is comfortable to wear and which can be easily cleaned and reused.

These and other objects of the present invention are attained by means of a male truss for producing and maintaining an erection during intercourse that includes a rigid linear member having an axially extended opening passing therethrough, the member having a length such that it spans laterally across the dorsal region of a penis. A loop passes through the opening in the member and is arranged to pass circumferentially around the penis to apply a downward pressure upon the rigid member that is sufficient to restrict the flow of blood through the dorsal vein of the penis back to the heart. Blood being supplied to the penis by the arteries is thus retained in the erectile tissue of the organ to cause and maintain an erection.

BRIEF DESCRIPTION OF THE DRAWINGS

For a better understanding of these and other objects of the present invention, reference shall be made herein to the following detailed description of the invention which is to be read in association with the accompanying drawings, wherein.

DESCRIPTION OF THE INVENTION

Figure 1:
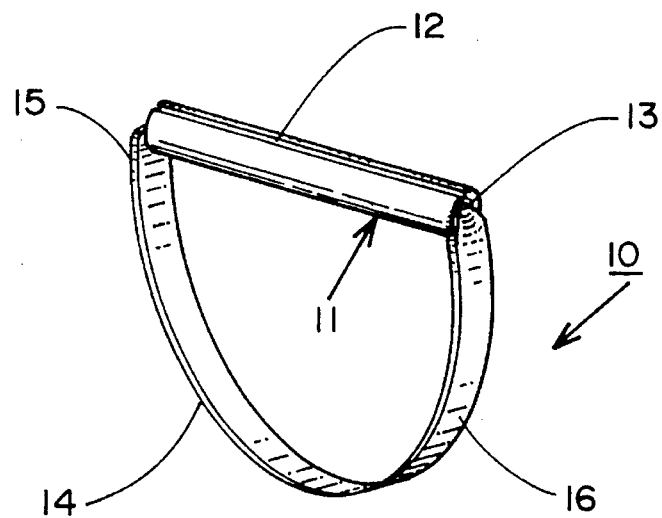
FIG. 1 is a perspective view illustrating a prior art embodiment of the invention.
Figure 3:
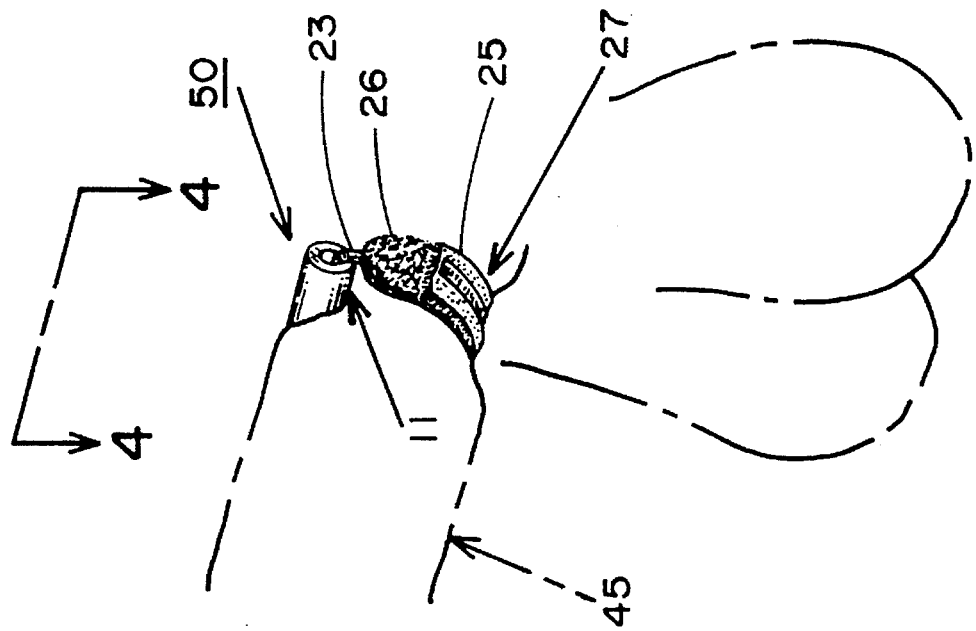
FIG. 3 is a perspective view showing another form of the prior art mounted upon a penis.

Referring initially to FIG. 1, there is shown a first embodiment of the present invention, generally referenced 10. The device 10 includes a rigid cylindrically shaped member 11 having an elongated, axially extended slit 12 passing through the side wall of the member which opens into a central hole 13 that passes axially through this member. An elastic loop 14 is passed into the cylinder through the slot. The section 15 of the loop that is housed within the cylinder has an axial width that is narrower than the free section 16 of the loop that is situated outside of the rigid cylinder. The circumference of the loop is less than the circumference of the penis during arousal so that it will exert a biasing force on the cylinder when the device is mounted upon the penis. In practice, the loop is expanded and the device is passed over the penis and the rigid cylinder is positioned over the dorsal region of the penis close to the base of the penis. When the device is positioned near or at the base of the penis, the expanded loop is allowed to contract into biasing contact around the penis thus drawing the rigid cylinder downwardly into pressure contact against the dorsal region of the penis as illustrated in FIG. 3. As will be described in greater detail below, sufficient pressure is exerted by the loop to cause the cylinder to restrict the flow of blood through the dorsal vein of the penis.

Figure 2:
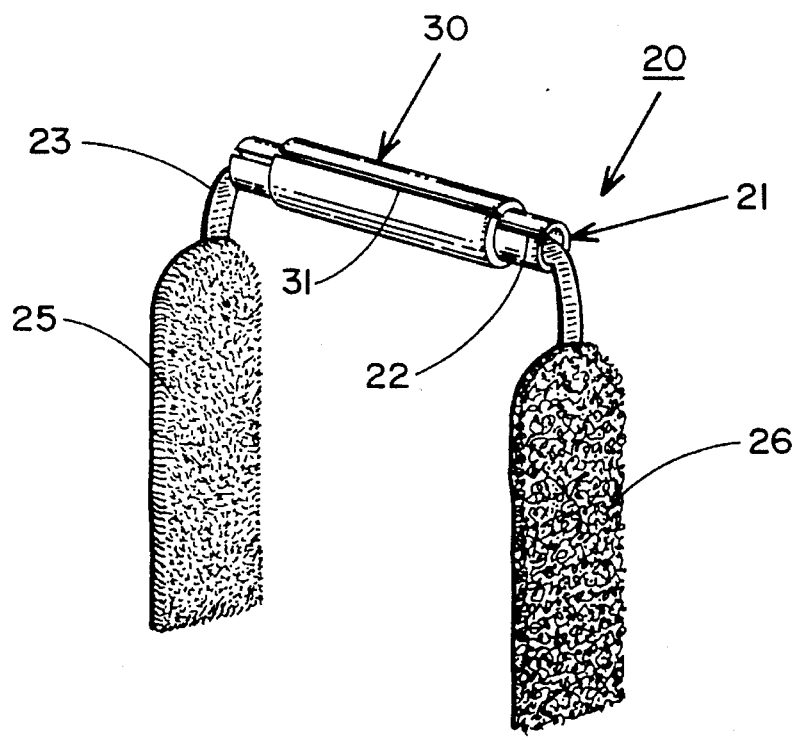
FIG. 2 is a perspective view further illustrating a second prior art embodiment of the invention.

Turning now to FIG. 2, there is shown a second embodiment of the present invention generally referenced 20. A first inner rigid cylinder 21 having an axially aligned slit 22 is passed over an elastic band 23. One end of the elastic band is attached to a hook pad 25 while the opposite end of the band is similarly attached to an eye pad 26. The two pads together form an adjustable Velcro-type closure device 27.

A second outer rigid cylinder 30, also containing an axially disposed slot 31 of sufficient width to allow either the hook or the eye pad to pass therethrough, is slidably mounted upon the inner cylinder as shown. The outer cylinder performs a first important function of closing the slot 21 of the inner cylinder thus preventing the elastic band 23 from inadvertently slipping out of the inner cylinder during use. The outer cylinder also serves a second function of allowing the outer diameter of the rigid section of the device to be selectively changed to fit the wearer. A number of outer cylinders, each having a different outer diameter, can be provided with each device. Through a minimal amount of experimentation, the user can thus select a cylinder diameter that is most satisfactory for his need. Accordingly, the device shown in FIG. 2 allows for two forms of adjustment. The first involves regulating the amount of tension applied to the rigid cylinder by loosening or tightening the closure device. The second involves the proper selection of the outer cylinder to obtain the greatest comfort, without sacrificing performance.

Turning now to FIG. 3, there is shown another form of the invention generally referenced 50 mounted at the base of penis 45. In this form of the invention, a single rigid cylinder 11, as explained above in reference to FIG. 1, is shown mounted upon an elastic band 23 as explained above with reference to FIG. 2. Here again, the ends of the band are attached to a Velcro closure device 25 and 26 which can be adjustably fastened as shown around the penis to apply the desired pressure to the cylinder. As should be evident from the drawing, the axial width of the closure pads is considerably greater than the contact zone of the cylinder. Accordingly, the downward biasing pressure concentrated in the cylinder contact region is more widely distributed over a greater area of the penis by the closure device thus providing for a more comfortable fit, and minimal interference with arterial blood entering to fill the organ.

Figure 4:
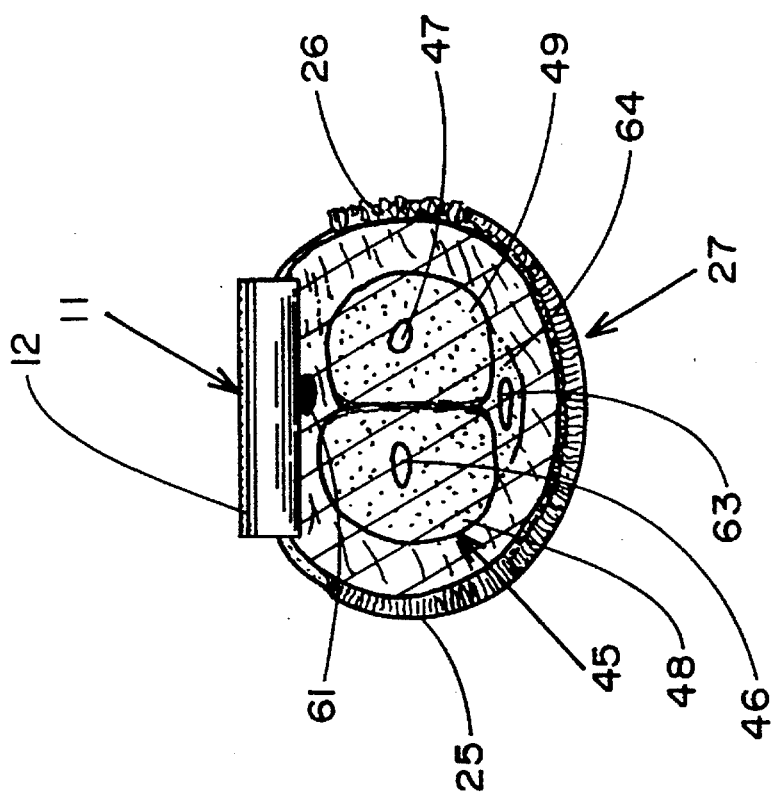
FIG. 4 is an enlarged section taken along lines 4—4 in FIG. 3 further illustrating the present invention in restricting contact with the dorsal vein of the penis.

Referring now to FIG. 4, there is illustrated a section taken along lines 4–4 in FIG. 3 showing the device 50 positioned upon penis 45. Blood from the heart enters the penis through two profunda arteries 46 and 47 and a pair or lesser dorsal arteries (not shown). The profunda arteries are surrounded by the corpus cavernosa 48 and 49. Normally, the blood circulates through the penis and is returned back to the heart through the dorsal vein 61. The urethra 63 is located in the lower part of the penis through which urine moves as it is being discharged from the body. The urethra, in turn, is surrounded by the corpus spongiosum 64 which like the corpus cavernosum is made up of erectlie tissue. The tissue contains little or no blood when the penis is in a non-erected state. The tissue, however, becomes filled with blood during an erection and the blood is trapped therein as long as the erection is maintained.

The device 50 is shown positioned upon the base of the penis in FIG. 4 with the rigid cylinder 11 located directly over the dorsal vein which, as noted above, functions to carry blood from the corpus cavernosum and corpus spongiosum regions back to the heart. The closure device 27 is passed about the base of the penis and is adjusted to the desired tension. The cylinder is thus pulled downwardly with sufficient pressure to occlude the dorsal vein and restrict the flow of blood from the corpus cavernosum and corpus spongiosum back to the heart. Blood flowing into the penis during arousal thus becomes entrapped in the erectlie tissue causing the tissue to swell thereby producing an erection.

Once the closure device is fastened, the elastic band 23 maintains a steady biasing force on the cylinder which is concentrated within the arcuate contact area between the cylinder and the dorsal region of the penis. Because the cylinder is rigid and the contact area between the cylinder and the penis is relatively narrow, the cylinder is able to penetrate the dorsal region to a depth that is relatively greater than other devices found in the prior art. Because the cylindrical member penetrates downwardly along a linear line of contact, it is not necessary that the device be precisely positioned in regard to the dorsal vein when being fitted on the penis. Simple placement of the cylinder close to the pubic bone is all that is necessary to produce the desired restriction of the dorsal veins. Because of the relatively small size of the device, positioning the device as explained will not interfere with the wearer's ability to perform intercourse. To clean the device, the cylinder or cylinders are simply removed and washed along with the elastic loop or closure device.

Figure 5:
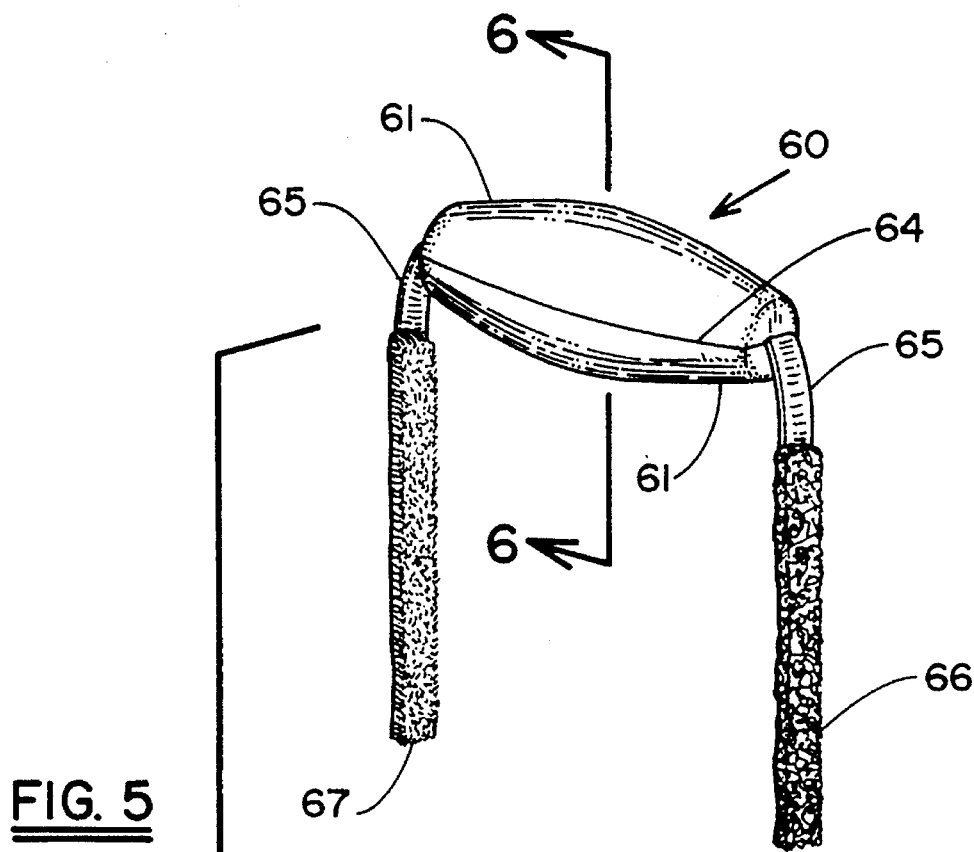
FIG. 5 is a perspective view illustrating a further embodiment of the present invention.
Figure 6:
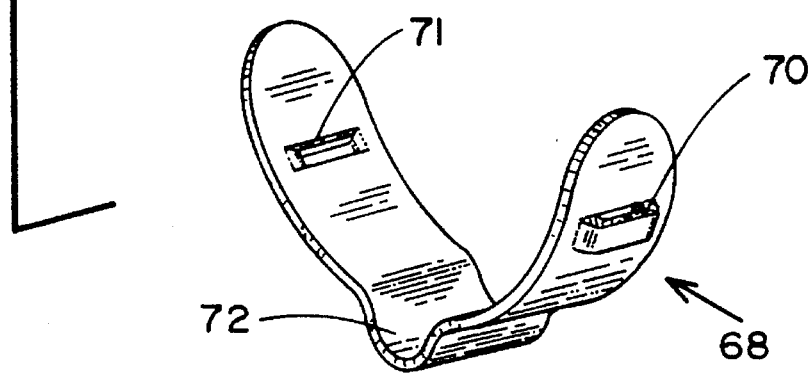
FIG. 6 is a sectional view taken along lines 6—6 in FIG. 5.
Figure 6:
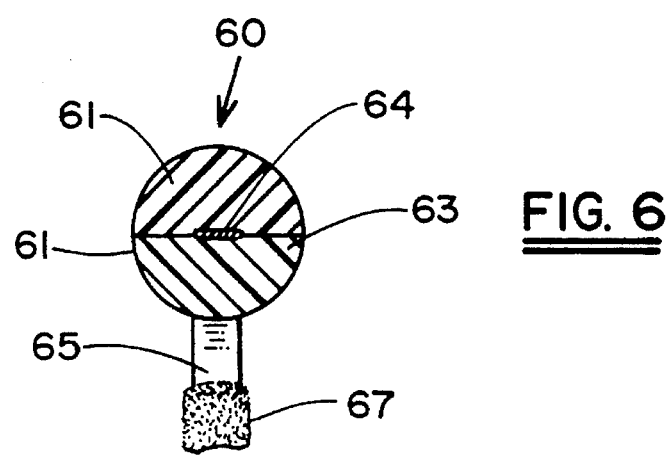
Figure 7:
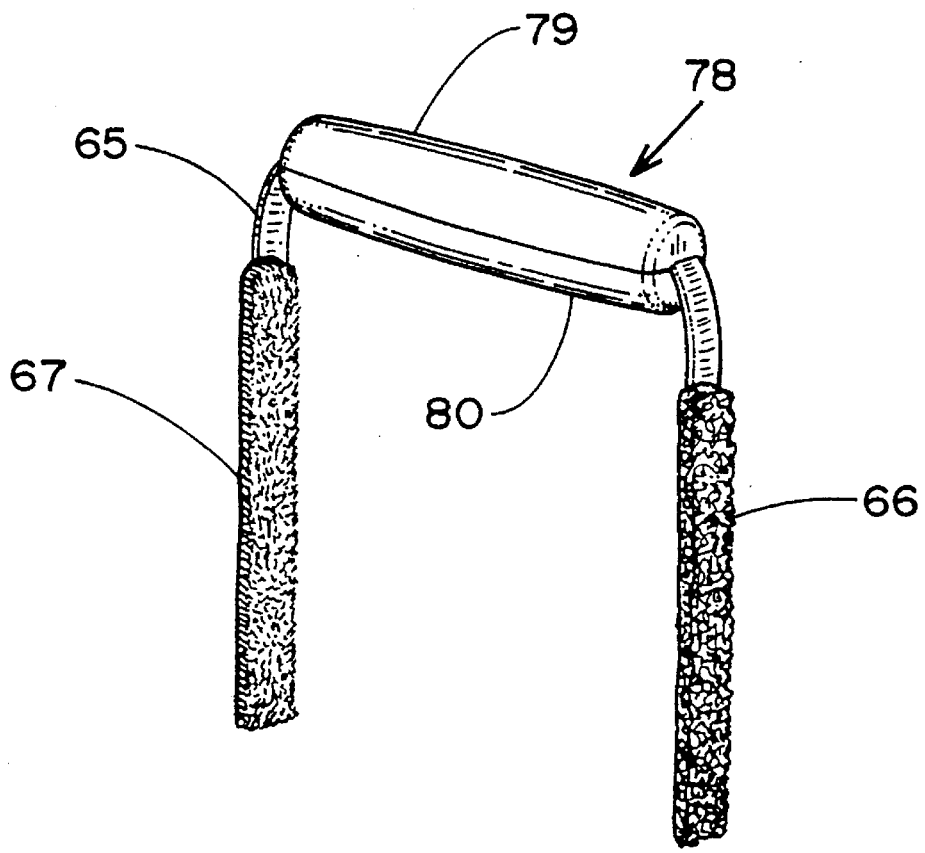
FIG. 7 is a perspective view of a still further embodiment of the present invention.

With further reference to FIGS. 5 and 6, there is shown another embodiment of the invention that includes an elongated tapered cylindrical member 60 that is formed by two rigid half sections 61—61 that are preferably molded from a suitable plastic material. The half sections are symmetrically formed along the longitudinal axis of the cylinder to establish two opposed planar surfaces along the line of joinder 63. Each planar surface contains a longitudinally disposed groove 64 into which an elastic strap 65 is seated.

The elastic strap 65 extends outwardly beyond two opposed ends of the cylindrical member. A hook pad 66 is secured by any suitable means to one end of the strap, while a loop pad 67 is secured to the other end of the strap. The two pads cooperate to form an adjustable Velcro type fastener that allows the truss to be pressure tightened about the penis as explained above to restrict the flow of blood through the dorsal vein back to the heart.

The two half sections are joined in assembly to securely lock the elastic strap therebetween. The half section can be adhesive bonded in assembly using a suitable epoxy resin, or heat bonded using well known thermal bonding techniques.

The truss is further equipped with an arcuate shaped bridge member 68 that generally complements the cross sectional shape of the penis. In this embodiment a pair of elongated rings 70 and 71 are mounted upon the two end sections of the bridge member so that the strap member can be passed therethrough. The mid-portion of the bridge member is provided with a convex section 72 which, in assembly, is positioned over the urethra which is located on the underside of the penis. The convex section is arranged to span the urethra region and thus relieve the pressure on the urethra as the cylindrical member is tightened down into occluding contact with the dorsal vein.

In this particular embodiment of the invention, the member 60 has an enlarged diameter at its midsection and a smaller diameter at each end section so that it tapers downwardly at a uniform angle from the midsection toward the two end sections. Preferably, the angle of taper is between 1° and 45°. The tapered geometry is designed to provide slightly greater pressure in the dorsal vein region than in the surrounding contact regions and thus deliver greater occluding pressure on the dorsal vein. With the use of the bridge, higher pressure can be applied to the dorsal region without adversely affecting ejaculation or the ability to gain and sustain an erection.

Turning now to FIGS. 7–10, there is shown still another embodiment of the invention. In this embodiment, the tapered cylindrical member shown in FIG. 5 is replaced by a cylinder 78 having a uniform cross section along its entire length. Here again, the cylinder is formed by two symmetrical half sections 79 and 80 that are joined in assembly to securely capture the strap 65 therebetween.

Figure 10:
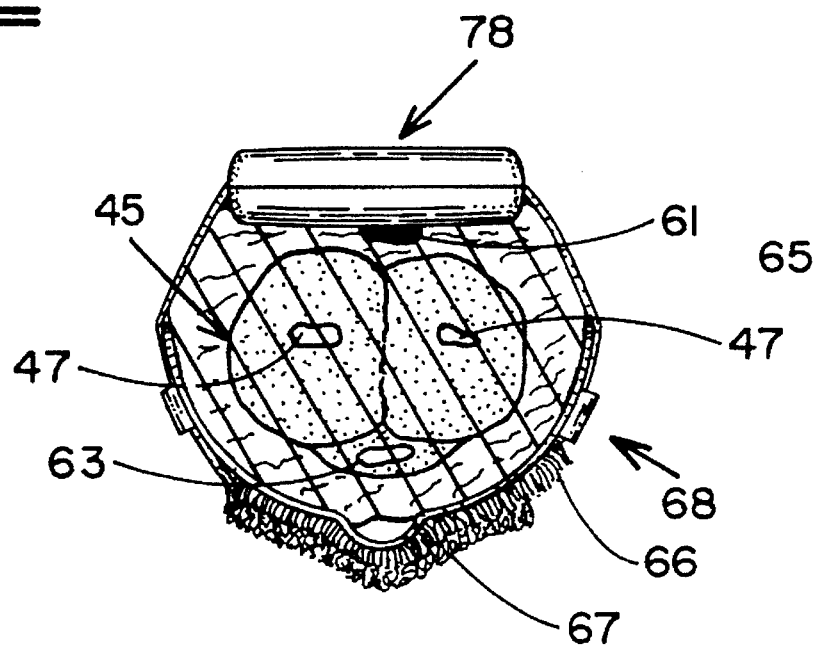
FIG. 10 is an enlarged sectional view taken along lines 10—10 in FIG. 9.
Figure 8:
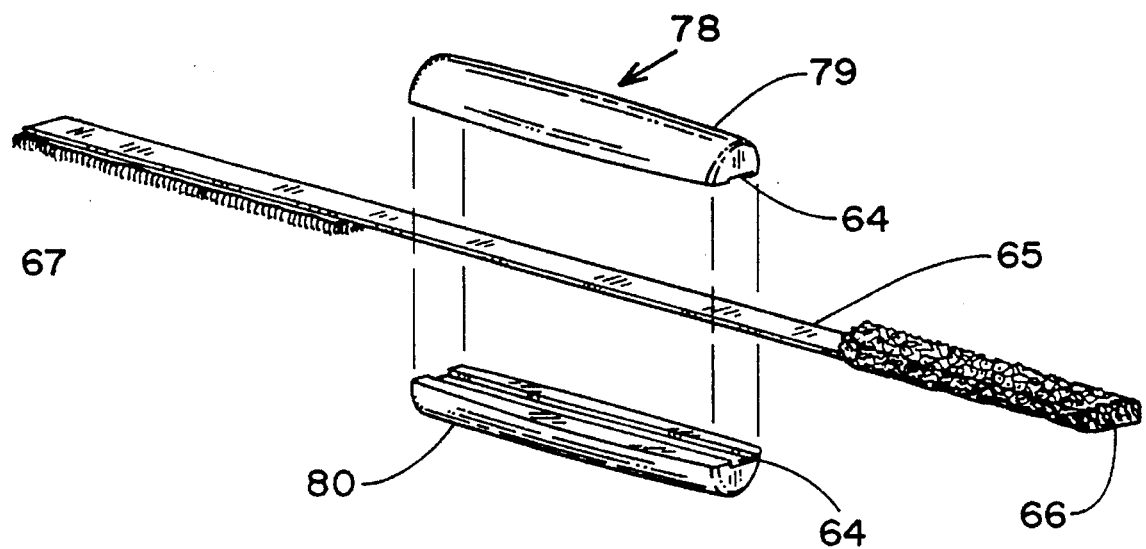
FIG. 8 is an exploded view in perspective showing the construction of the embodiment of the invention shown in FIG. 7.
Figure 9:
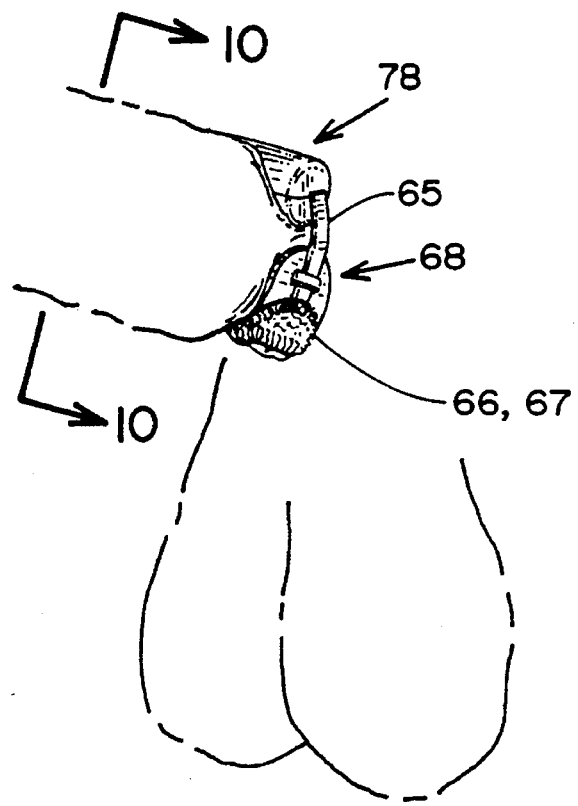
FIG. 9 is a perspective view of the device shown in FIG. 7 mounted in pressure contact over the dorsal vein and the urethra of the penis.

FIGS. 9 and 10 show the truss mounted at the base of the penis with the cylindrical member tightly compressed against the upper section thereof. As explained above, because of the construction of the cylinder, the user is not required to accurately place the cylindrical member directly upon the dorsal vein, but can simply mount it as shown for effective results. The bridge member 68 is also shown as part of the assembly with the convex section spanning the urethra. The two members are tightened against the penis using the adjustable fastener to insure a snug, yet comfortable fit. Through some experimentation, the user can quickly determine the proper amount of pressure that can be applied to effectively restrict the flow of blood back to the heart.

Figure 11:
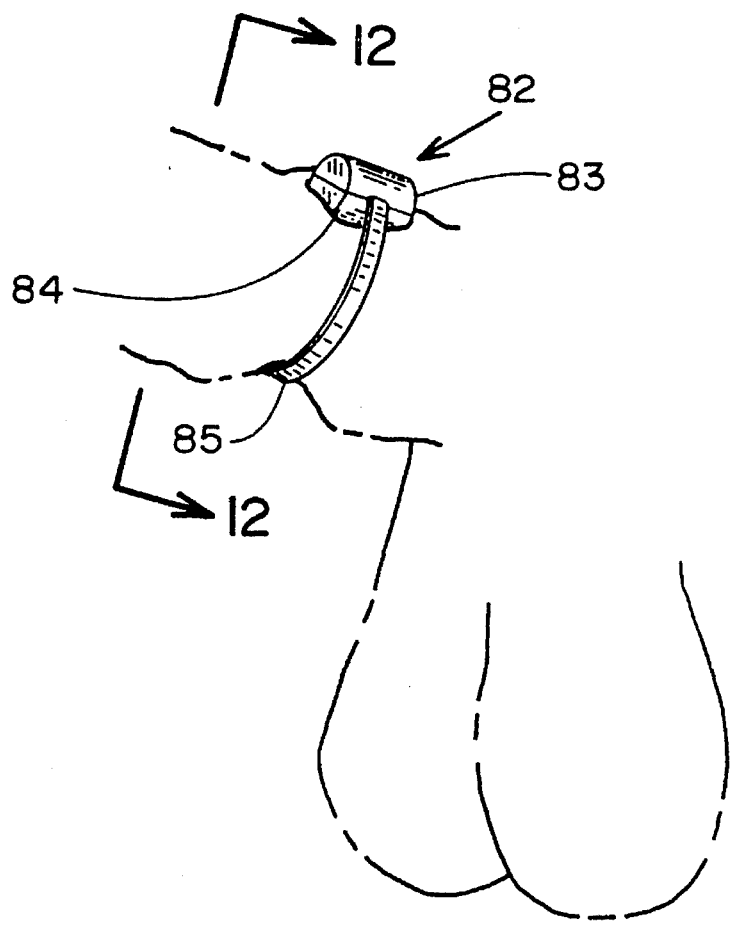
FIG. 11 is a perspective view of a still further embodiment of the present invention.
Figure 12:
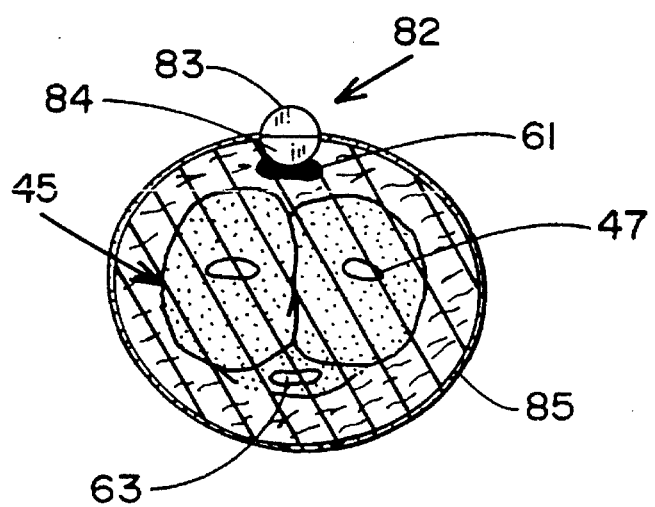
FIG. 12 is an enlarged sectional view taken along lines 12—12 in FIG. 11.

FIGS. 11 and 12 depict a further embodiment of the invention wherein the truss includes a foreshortened cylindrical compression member 82 having two half symmetrical half sections 83 and 84. In this embodiment, an elastic endless loop 85 is captured between the half sections as described above. The loop, however, passes through the midsection of the cylinder along a diametric radial of the cylinder. Again, the cylinder is mounted on the upper side of the penis over the dorsal vein and the loop is adapted to apply sufficient pressure to occlude the dorsal vein. Here again, because of the geometry of the cylindrical member, precise positioning of the member is not necessary. If the member is slightly offset with regard to the dorsal vein, the member will, at some point, cross the vein in some region to apply the desired pressure.

Although this latter embodiment is shown equipped with an elastic loop, it should be evident the band can be replaced by an elastic strap, a Velcro fastener combination, and a bridge member can also be mounted on the device as noted above.

While this invention has been explained with reference to the structure disclosed herein, it is not confined to the details set forth and this invention is intended to cover any modifications and changes as may come within the scope of the following claims:

What is claimed is:

1. A male truss for assisting in producing and maintaining an erection that includes
    an elongated cylindrical member divided along its central longitudinal axis into two rigid half sections,
    a loop means mounted between the two half sections that is arranged to pass around the circumference of a penis to apply pressure to the cylindrical member to draw said member against the dorsal region of the penis to restrict the flow of blood through the dorsal vein of the penis, and
    means to join together the two rigid half sections of the cylindrical member to entrap the loop therebetween.

2. The male truss member of claim 1 wherein said cylindrical member has a uniform diameter along its entire length.

3. The male truss member of claim 1 wherein said cylindrical member has a larger diameter at its midsection and a smaller diameter at its two end sections whereby the member tapers downwardly at a uniform angle from the midsection toward the two end sections.

4. The male truss member of claim 3 wherein said angle of the taper is between 1° and 45°.

5. The male truss member of claim 1 wherein said loop is positioned along the longitudinal central axis of said cylindrical member.

6. The male truss member of claim 1 wherein said loop is positioned along a diametrical axis of the cylindrical member.

7. The male truss member of claim 1 wherein said loop is an endless elastic band.

8. The male truss member of claim 1 wherein said loop includes a strap that extends from either side of said cylindrical member and a fastening means mounted on either end of said strap for cojoining the ends of said strap.

9. The male truss member of claim 8 wherein said fastening means further includes a loop pad secured to one end of the strap and a hook pad secured to the other end of said strap.

10. The male truss member of claim 1 that further includes an arcuate shaped bridge member attached to the loop opposite the cylindrical member, said arcuate shaped member further including a centrally located raised section that is arranged to form a bridge over the urethra of the penis to relieve the pressure on the urethra when the truss is mounted upon the penis.

11. The male truss member of claim 10 wherein said bridge member contains further means for removably attaching said bridge member to said loop.

12. The male truss member of claim 1 wherein the two half sections are cojoined by an adhesive.

13. The male truss member of claim 1 wherein the two half-sections are formed of plastic and are thermal bonded in assembly.

* * * * *